US010259668B2

(12) United States Patent
Yamamoto (10) Patent No.: US 10,259,668 B2
(45) Date of Patent: Apr. 16, 2019

(54) APPARATUS OF FEEDING WORKPIECES WITH A MESH DRUM (71) Applicant: NHK SPRING CO., LTD., Yokohama-shi, Kanagawa (JP)

(72) Inventor: Asato Yamamoto, Kanagawa (JP)

(73) Assignee: NHK Spring Co., Ltd., Kanagawa (JP)

( * ) Notice: Subject to any disclaimer, the term of this patent is extended or adjusted under 35 U.S.C. 154(b) by 0 days.

(21) Appl. No.: 15/938,720

(22) Filed: Mar. 28, 2018

(65) Prior Publication Data
US 2018/0290843 A1 Oct. 11, 2018

(30) Foreign Application Priority Data

Apr. 7, 2017 (JP) .................... 2017-77062

(51) Int. Cl.
*B65G 47/12* (2006.01)
*B65G 47/32* (2006.01)
*B65G 65/23* (2006.01)
*G01N 35/04* (2006.01)

(52) U.S. Cl.
CPC ............. *B65G 65/23* (2013.01); *B65G 47/12* (2013.01); *B65G 47/32* (2013.01); *G01N 35/04* (2013.01)

(58) Field of Classification Search
CPC ...... B65G 47/32; B65G 47/12; B65G 47/428; B65G 47/1435; G01N 35/07
USPC ........................................................ 198/443
See application file for complete search history.

(56) References Cited

U.S. PATENT DOCUMENTS

| 3,589,531 | A | * | 6/1971 | Povlacs | G06M 1/00 198/443 |
| 3,734,000 | A | * | 5/1973 | Ziener | A22C 17/04 100/121 |
| 3,926,147 | A | * | 12/1975 | Steube | C23C 14/223 118/418 |
| 4,485,526 | A | * | 12/1984 | Opanasenko | A22C 25/02 452/99 |
| 6,367,611 | B1 | | 4/2002 | Kuenzler et al. | |
| 6,449,876 | B1 | * | 9/2002 | Pursell | D06F 58/02 34/108 |
| 2004/0052702 | A1 | * | 3/2004 | Shuman | A23L 3/003 422/208 |
| 2012/0261232 | A1 | | 10/2012 | Nakajima et al. | |

(Continued)

FOREIGN PATENT DOCUMENTS

| JP | 63-192323 U | 12/1988 |
| JP | 2-75415 U | 6/1990 |
| JP | 2000-238912 A | 9/2000 |

(Continued)

*Primary Examiner* — James R Bidwell
(74) *Attorney, Agent, or Firm* — Norris McLaughlin, P.A.

(57) ABSTRACT

The present invention provides an apparatus of feeding workpieces, capable of preventing generated contaminants from adhering workpieces and improving stabilization in a discharge rate of the workpieces while having advantage of the drum type. The apparatus has a mesh drum, a rotary drive and an angle adjuster. The mesh drum has a mesh circumferential wall that defines a space for accommodating workpieces, the mesh drum is configured to be rotated and tilted by the rotary drive and the angle adjuster. The mesh drum has a mesh size of the mesh circumferential wall being set according to form of the workpieces to ensure the separating of the workpieces.

1 Claim, 7 Drawing Sheets (56) References Cited

U.S. PATENT DOCUMENTS

2014/0346092 A1* 11/2014 Kimura .................. E01H 12/00
 209/235
2015/0104350 A1* 4/2015 Schacher ........... B65G 47/1428
 422/63

FOREIGN PATENT DOCUMENTS

| JP | 2001-277051 A | 10/2001 |
| JP | 2002-154639 A | 5/2002 |
| JP | 2003-095420 A | 4/2003 |
| JP | 2003-155112 A | 5/2003 |
| JP | 2012-218930 A | 11/2012 |
| JP | 2007-269484 A | 10/2017 |

* cited by examiner

APPARATUS OF FEEDING WORKPIECES WITH A MESH DRUM

BACKGROUND OF THE INVENTION

1. Field of the Invention

The present invention relates to an apparatus of feeding workpieces while separating the same.

2. Description of the Related Art

In a production line to assemble fine parts, an automatically aligning and feeding apparatus or a part feeder is frequently used to feed fine workpieces.

For example, a part feeder is used to feed base plates in assembly of a head suspension to be incorporated in a hard disk drive.

For such a head suspension, higher cleanliness is required as higher density and higher capacity of a recent hard disk drive and even particles generated in a production line thereof are non-negligible.

In view of the situation, there are part feeders proposed in, for example, JP2000-238912A and JP2003-095420A capable of reducing particles. It is, however, hard for those part feeders to prevent intermittently rubbing and hitting between workpieces accommodated in a vibration bowl.

To cope with this problem, there is a workpiece feeder disclosed in JP2012-218930 as a part feeder proposed by the applicant of this application. The workpiece feeder does not apply continuous fine vibration to workpieces and therefore prevents intermittently rubbing and hitting between the workpieces.

The workpiece feeder has a part charge box to accommodate the workpieces and discharge a given rate of the accommodated workpieces to a feeder stage. The part charge box has a simple structure so that the discharge rate of the workpieces is not stable.

In this regard, there are different types of conventional hoppers including a drum type, an inclined feed path type, a linear vibration type, a belt conveying type and the like.

The drum type is as disclosed in JP63-192323U, JP02-075415U, JP2001-277051A, JP2002-154639A, JP2003-155112A, and JP2007-269484A. The inclined feed path type has a slide guide provided at an outlet of a hopper to discharge workpieces through the slide guide. The linear vibration type discharges workpieces by vibration and a slight tilt of a hopper. The belt conveying type has a belt arranged at a bottom of a hopper and drives the belt to discharge workpieces little by little.

When fine workpieces are discharged by a small amount at a fixed rate, the linear vibration type is relatively advantageous. The linear vibration type, however, involves the vibration and is likely to cause fine scratches on the workpieces.

The drum type has a helical blade on an inner surface of a drum. The drum type rotates the drum to guide and extrude the workpieces with the blade, thereby to discharge workpieces by a small amount at a fixed rate (discharge rate) to the feeder stage. The drum type operates silently, is superior in discharge of the workpieces, and does not cause fine scratches on the workpieces unlike the linear vibration type and the like.

On the other hand, the drum type generates contaminants, fine particles or the like during the rotation of the drum and accumulates the same on the bottom of the drum and/or the blade. This causes the accumulated contaminants to adhere to the workpieces.

Further, since the drum type extrudes the workpieces with the blade, a number of workpieces are frequently discharged as a clump while being laid one on another. This limits on stabilization in the discharge rate of the workpieces.

SUMMARY OF THE INVENTION

An object of the present invention is to provide an apparatus of feeding workpieces, capable of preventing generated contaminants or fine particles from adhering workpieces and improving stabilization in a discharge rate of the workpieces while having advantage of the drum type.

In order to accomplish the object, an aspect of the present invention provides an apparatus of feeding workpieces, having a mesh drum, a rotary drive and an angle adjuster. The mesh drum has a mesh circumferential wall that defines a space for accommodating workpieces, the mesh drum rotatably and tiltably supported with an apparatus base to separate and discharge the workpieces. The rotary drive is what drives the mesh drum to be rotated. The angle adjuster is what drives the mesh drum to be tilted. The mesh drum has a mesh size of the mesh circumferential wall being set according to form of the workpieces to ensure the separating of the workpieces.

According to the aspect, the mesh drum rotates and tilts to discharge workpieces therefrom while having advantage of the drum type. Further, the rotating mesh drum causes a workpiece laid on another workpiece to slide down in a rotation direction of the mesh drum while suppressing a workpiece contacting the mesh of the mesh drum from sliding in the rotational direction. This separates or disperses the workpieces to improve stabilization of a discharge rate of the workpieces from the mesh drum. Contaminants, fine particles or the like generated during the rotation of the mesh drum pass through the mesh of the mesh drum to be removed outside from the mesh drum. This prevents the contaminants from adhering the workpieces.

DETAILED DESCRIPTION OF EMBODIMENTS

An embodiment according to the present invention provides a part feeder as an apparatus of feeding workpieces, capable of preventing generated contaminants, fine particles or the like from adhering workpieces and improving stabilization in a discharge rate of the workpieces while having advantage of the drum type.

The part feeder has a mesh drum driven by a stepping motor of a rotary drive and a stepping motor of an angle adjuster to be rotated and tilted, thereby to separate or disperse workpieces and discharge the same from the mesh drum. The mesh drum includes a mesh circumferential wall that defines a space for accommodating the workpieces to be discharged. A mesh size of the mesh circumferential wall is set according to form of the workpieces to ensure the separating of the workpieces.

The mesh drum is detachably supported with an apparatus base. For this, in the embodiment, the part feeder includes a drum base being a part rotatably and tiltably connected to the apparatus base and driven by the rotary drive and the angle adjuster. The detachably supporting of the mesh drum is performed so that the drum base encloses the mesh drum while maintaining an airgap between the mesh drum and the drum base. Then, an opening of the mesh drum is fixed to an opening of the drum base using an engagement/disengagement part.

Hereinafter, the embodiment of the present invention will be explained in detail with reference to drawings.

Figure 1:
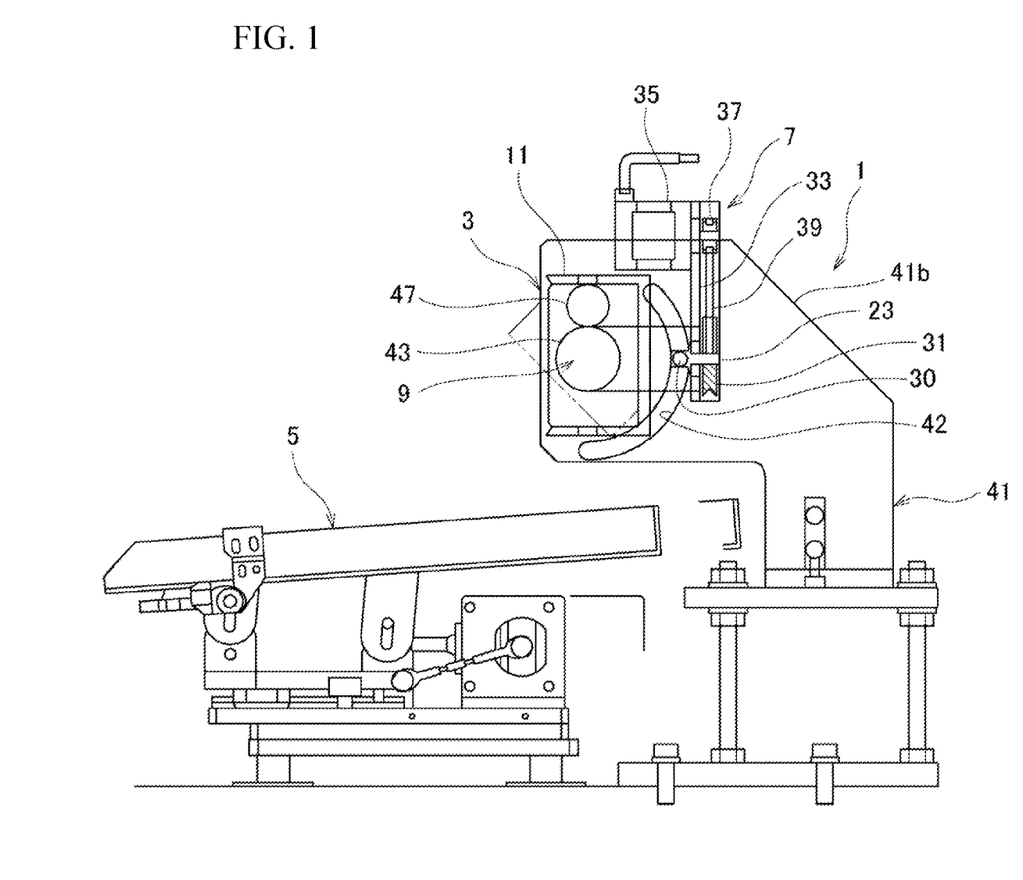
FIG. 1 is a schematic side view illustrating a part feeder according to a first embodiment of the present invention.
Figure 2:
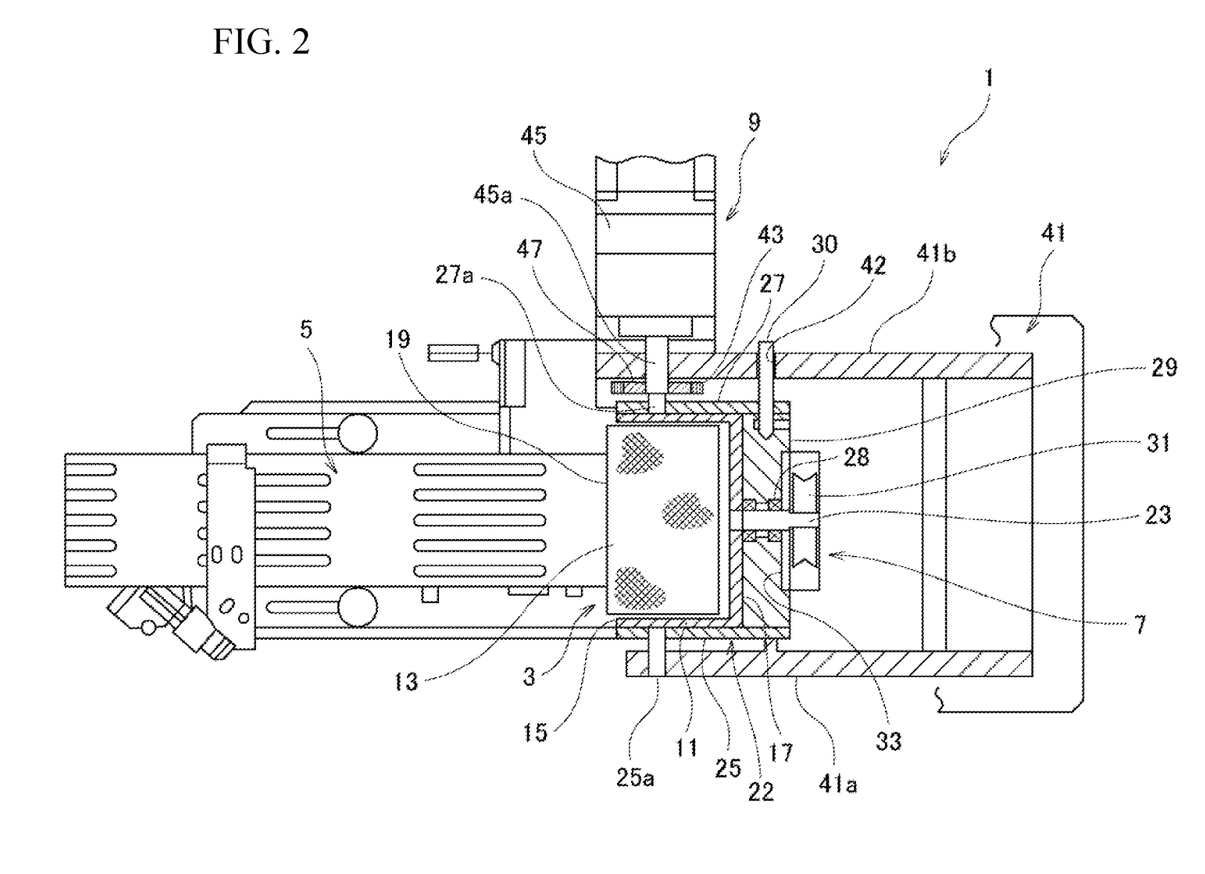
FIG. 2 is a schematic plan view illustrating the part feeder of FIG. 1.
Figure 3:
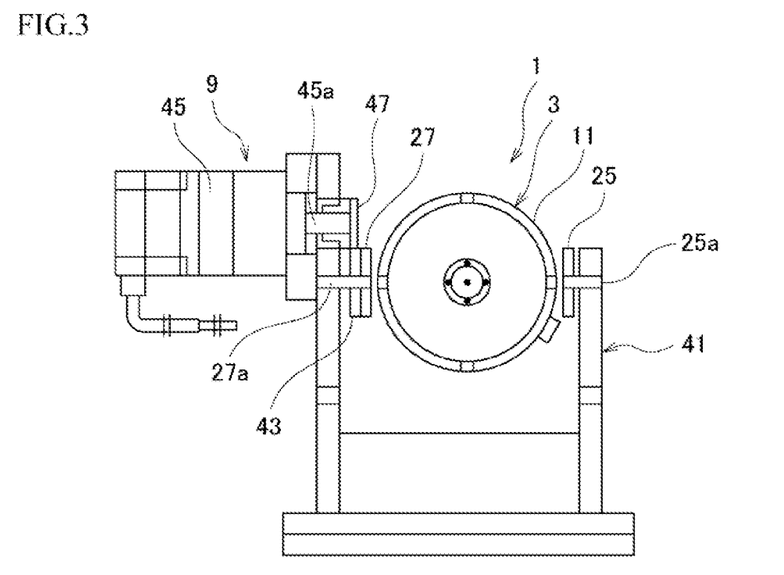
FIG. 3 is a schematic front view of the part feeder of FIG. 1.
Figure 4:
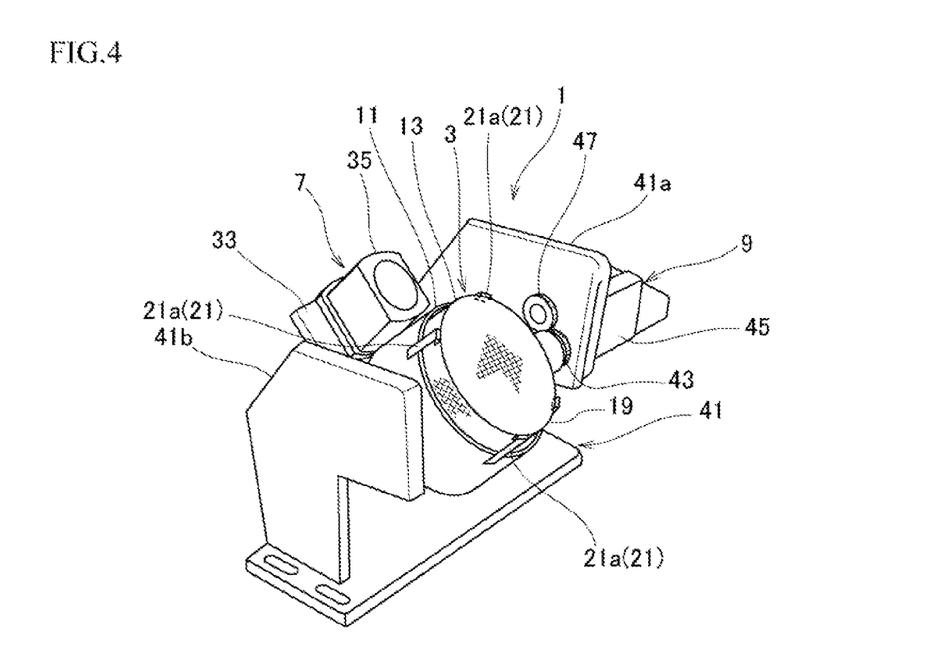
FIG. 4 is a perspective view illustrating a drum part of the part feeder and the supporting structure thereof according to the embodiment.

FIG. 1 is a schematic side view illustrating the part feeder, FIGS. 2-3 are a schematic plan view and a schematic front view illustrating the same, and FIG. 4 is a perspective view illustrating a drum part of the part feeder and the supporting structure thereof.

As illustrated in FIGS. 1-4, the part feeder 1 is an apparatus of feeding workpieces while separating or dispersing the same. According to the embodiment, the workpieces or parts are base plates for a head suspension incorporated in a hard disk drive. The part feeder 1 may handle other types of fine workpieces.

The part feeder 1 has a drum part 3 and a feeder stage 5 being a stage to which the workpieces are fed.

The drum part 3 is configured to discharge the workpieces by a small amount at a fixed rate (discharge rate) to the feeder stage 5. To realize such discharge, the drum part 3 is driven by the rotary drive 7 and the angle adjuster 9 to separate the workpieces or the base plates and discharge the same. The drum part 3 of the embodiment has the drum base 11 and the mesh drum 13.

The drum base 11 is a part rotatably and tiltably connected to the apparatus base 41 and driven by the rotary drive 7 and the angle adjuster 9. The drum base 11 is made of metal such as stainless steel and formed into a bottomed cylindrical shape with an opening 15 and a bottom 17.

The mesh drum 13 is formed into a bottomed cylindrical shape straightly extending along an axis thereof with a constant outer diameter. The outer diameter of the mesh drum 13 is smaller than an inner diameter of the drum base 11. The bottom side of the mesh drum 13 is enclosed in the drum base 11. The mesh drum 13 is not limited to the straightly extending cylindrical shape and may be tapered or have one or more steps according to changes in the outer diameter.

The mesh drum 13 is detachably supported with the apparatus base 41. According to the embodiment, the mesh drum 13 is detachably held by the drum base 11 connected to the apparatus base 41 while maintaining a circumferential airgap between the mesh drum 13 and the drum base 11. This holding is performed by an engagement/disengagement part 21 provided at the opening 15 of the drum base 11. With this holding, the engagement/disengagement part 21 fixes the opening 19 of the mesh drum 13 to the opening 15 of the drum base 11.

The engagement/disengagement part 21 has arms 21a circumferentially arranged around the opening 15 of the drum base 11. Each arm 21a is a plate spring which base end is fixed to the drum base 11 and protrudes from the opening 15 of the drum base 11 in a direction along a rotation axis of the drum base 11. A front end of the arm 21a has a hook shape folded back toward the base end and elastically contacts an outer surface of the mesh drum 13 around the opening 19.

Accordingly, the mesh drum 13 is pressed into the drum base 11 against the elastic force of the arms 21a of the engagement/disengagement part 21, thereby to be detachably attached to the drum base 11.

In this attached state, the bottom of the mesh drum 13 is spaced apart from the bottom of the drum base 11 to define an axial airgap. The bottom of the mesh drum 13 may be contacted and supported with the bottom of the drum base 11.

The mesh drum 13 enclosed in and supported with the drum base 11 is driven to be rotated and tilted together with the drum base 11 to discharge the workpieces.

The drum base 11 is connected to the apparatus base 41 through a movable bracket 22. Namely, the bottom of the drum base 11 is connected to a rotary drive shaft 23. The rotary drive shaft 23 is supported with the movable bracket 22.

The movable bracket 22 includes right and left plates 25 and 27, and a base block 29. The right and left plates 25 and 27 are fixed at ends to respective right and left ends of the base block 29. To the base block 29, a guide shaft 30 is fixed.

The rotary drive shaft 23 is rotatably supported with the base block 29 through bearings 28. An outer end of the rotary drive shaft 23 protrudes outside from the base block 29 and a driven pulley 31 is attached to the outer end of the rotary drive shaft 23. The base block 29 has an attachment plate 33 fixed to the outer face of the base block 29 from which the rotary drive shaft 23 protrudes outside. The attachment plate 33 is elongated to have a free end radially distal to the base block 29. On the free end of the attachment plate 33, the stepping motor 35 is supported.

The stepping motor 35 has a driving pulley 37 on an output shaft thereof. A belt 39 is wound around the driving pulley 37 and the driven pulley 31.

The right and left plates 25 and 27 of the movable bracket 22 have support shafts 25a and 27a attached at respective front ends thereof. The support shafts 25a and 27a are rotatably supported with right and left support wall 41a and 41b of the apparatus base 41, respectively.

The right support wall 41b has a guide hole 42 with which the guide shaft 30 of the base block 29 is engaged to be guided along the guide hole 42.

The support shaft 27a has a driven gear 43 attached thereto. The stepping motor 45 of the angle adjuster 9 is attached to an outer face of the right support wall 41b of the apparatus base 41. The apparatus base 41 may have a different shape.

The output shaft 45a of the stepping motor 45 is passed through and inwardly protruded from the right support wall 41b toward the driven gear 43. The output shaft 45a has a driving gear 47 attached thereto. The driving gear 47 meshes with the driven gear 43.

When the stepping motor 35 of the rotary drive 7 is operated, rotationally driving force is output from the output shaft of the stepping motor 35. The rotationally driving force is transmitted from the driving pulley 37 on the output shaft through the belt 39 to the driven pulley 31 on the rotary drive shaft 23.

With the transmitted rotationally driving force, the rotary drive shaft 23 is rotated so that the drum base 11 is driven to be rotated. When the drum base 11 is rotated, the mesh drum 13 is integrally coaxially rotated together with the drum base 11.

When the stepping motor 45 of the angle adjuster 9 is operated, rotationally driving force is output from the output shaft 45a of the stepping motor 45. The rotationally driving force is transmitted from the driving gear 47 on the output shaft 45a to the driven gear 43 on the support shaft 27a.

With the transmitted rotationally driving force, the support shaft 27a is rotated so that the movable bracket 22 is driven to be tilted around the right and left support shafts 25a and 27a. When the movable bracket 22 is tilted, the mesh drum 13 is integrally tilted together with the drum base 11.

In this way, the rotary drive 7 and the angle adjuster 9 drives the mesh drum 13 to be rotated around the axis and tilted vertically.

According to the embodiment, the mesh drum 13 is gradually tilted while axially rotating, thereby to discharge the workpieces or base plates by a small amount at a fixed rate to the feeder stage 5.

Figure 5:
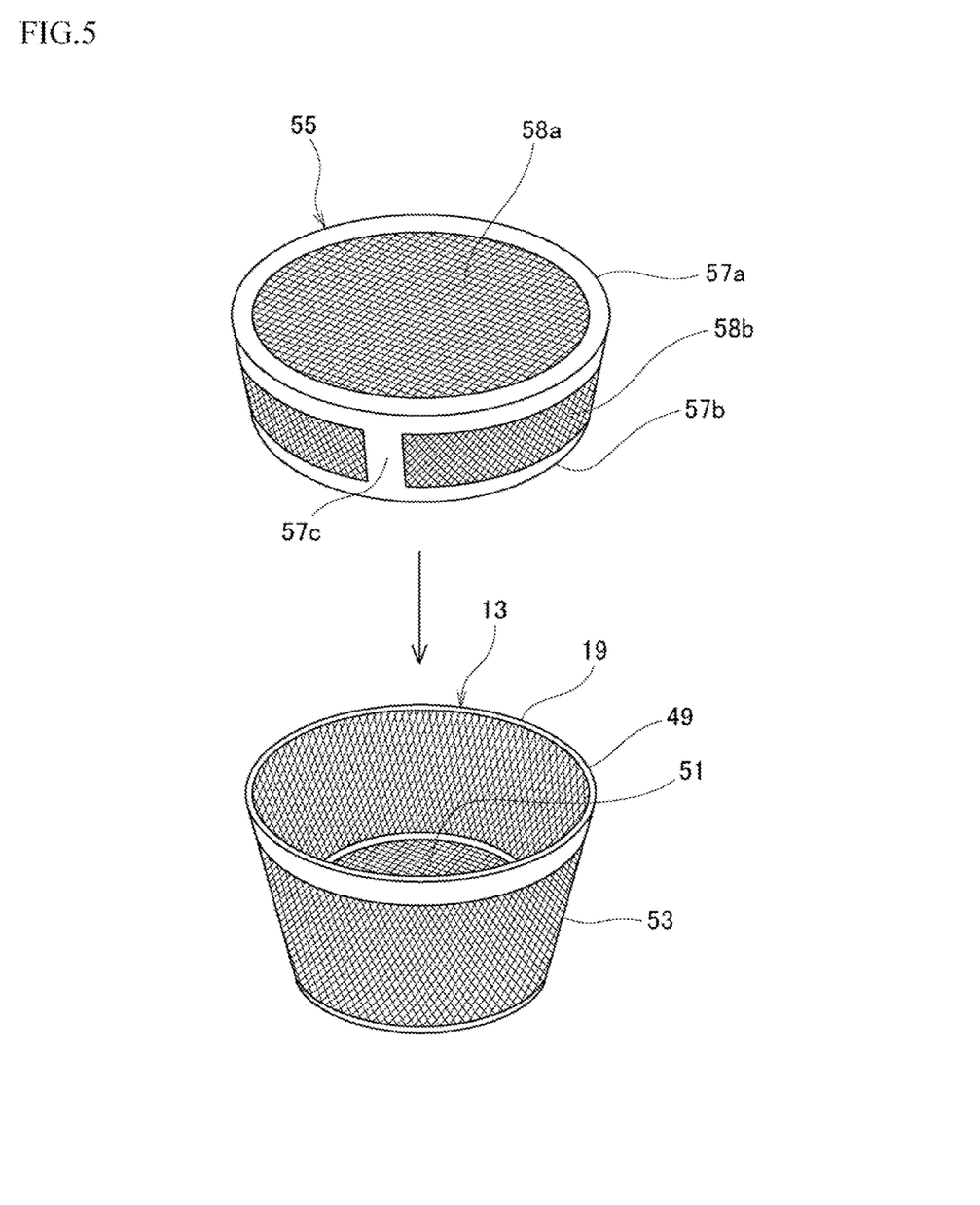
FIG. 5 is a perspective view illustrating a mesh drum used in the drum part and a cover for the mesh drum according to the embodiment.

FIG. 5 is a perspective view illustrating the mesh drum 13 and a cover 55 for the mesh drum 13.

The mesh drum 13 of FIG. 5 has a cap 49 made of metal such as stainless steel and defining the opening 19. The cap 49 is a part with which the arms 21a of the engagement/disengagement part 21 of the drum base 11 elastically contact at the front ends thereof. The mesh bottom 51 and the mesh circumferential wall 53 of the mesh drum 13 are made of metal mesh, net or netlike member such as stainless steel mesh. The mesh bottom 51 is flat. The bottom of the mesh drum 13 is not limited to the mesh bottom 51, but may be formed into a solid bottom without mesh openings. The mesh circumferential wall 53 is formed into a cylindrical shape with a constant outer diameter and defines inside a space accommodating the workpieces.

The mesh size of the mesh circumferential wall 53 is set according to form of the workpieces to ensure the separating of the workpieces. The form of the workpieces includes at least any one or all of the size, the thickness, the outer planer shape, the friction coefficient and the like. According to the embodiment, the mesh size is set according to the size of the workpiece.

The mesh size is set so that part of the workpiece does not enter into a mesh opening of the mesh drum 13. The mesh of the mesh drum 13 increases a friction coefficient of an inner circumferential surface of the mesh drum 13 relative to the workpiece compared with a smooth inner circumferential surface of a conventional drum. The friction coefficient of the inner circumferential surface is naturally higher than of the smooth inner circumferential surface in a case of the same material.

The friction coefficient of the inner circumferential surface is confirmable through a method like a surface friction test (KIP T 0903) for the mesh of the over 55. In this method, a friction coefficient is measured using test pieces each being the same as the workpiece. If the measured friction coefficient is higher than a friction coefficient between the workpieces, it is acceptable. Namely, the friction coefficient between the mesh drum 13 and the workpiece is higher than the friction coefficient between the workpieces.

When using the mesh drum 13 as a cleaning basket for the base plates as the workpieces, the mesh size of the mesh drum 13 is set so that each mesh opening or aperture of the mesh is about 0.39 mm in a wire mesh having a wire diameter of 0.25 mm and an open area of 36.8% (about #40 mesh) or less. The mesh openings less than about 0.39 mm (#40 mesh) may be set according to ultrasonic cleaning. It should be noted that a too small mesh opening may prevent an ultrasonic wave from passing through the mesh drum 13.

In a case where the mesh drum 13 is not used as the cleaning basket, the mesh size may be set regardless of whether the ultrasonic wave passes through the mesh drum 13.

The mesh openings may have a size lager than about 0.39 mm (#40 mesh) as long as part of the workpiece does not enter into the mesh opening of the mesh drum 13. Typically, the mesh opening is set to about 5-10% of the size of the workpiece in a plan view. In the case of the mesh drum 13 being used as the cleaning basket, the lower limit of the mesh opening of the mesh drum 13 is about 2% of the size of the workpiece in a plan view.

In this way, the mesh drum 13 is set so as to properly catch the workpieces with the mesh while preventing the mesh from being clogged with and excessively sliding the workpieces.

With this setting, the mesh drum 13 rotates to separate or disperse the workpieces on the inner circumferential surface thereof and discharge the same therefrom by a small amount at a fixed rate to the feeder stage 5.

When using the mesh drum 13 as the cleaning basket, the cover 55 is used. The cover 55 has upper and lower rings 57a and 57b and connections 57c as a frame made of, for example, stainless steel. The connections 7c connecting the upper and lower rings 57a and 57b. The cover 55 includes a top wall 58a attached to the upper ring 57a and a circumferential wall 58b attached between the upper and lower rings 57a and 57b. The top wall 58a and the circumferential wall 58b are made of metal mesh such as stainless steel mesh.

The cover 55 has a size to be fitted to the cap 49 of the mesh drum 13 and close the opening 19 of the mesh drum 13. In addition, the cover 55 does not contribute the discharge of the workpieces and may have a mesh size of the top wall 58a and the circumferential wall 58b that are different from the mesh size of the mesh drum 13.

FIGS. 6A to 6D are plan views illustrating different types of base plates, respectively.

Figures 6A, 6C:
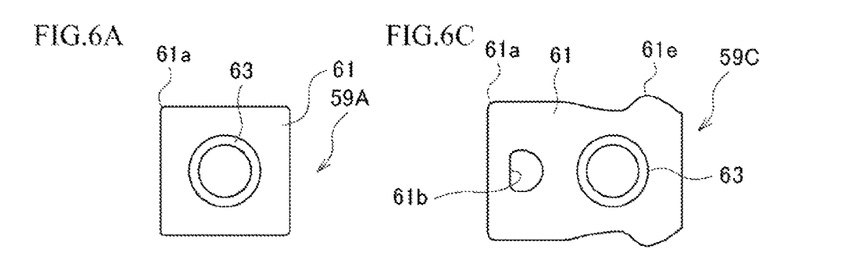
FIGS. 6A to 6D are plan views illustrating different types of base plates according to the embodiment.

As illustrated in FIG. 6A, the base plate 59A has a plate body 61 and a boss 63. The boss 63 is protruded from one side of the plate body 61. The boss 63 is to be inserted and fixed in to a hole formed through an arm of a carriage. With the inserting and fixing, the base plate 59A is fitted to the arm to perform attachment of a head suspension.

The base plate may have different shapes according to a size, a function or the like of a head suspension. For the workpiece of this embodiment, base plates as variations are exemplified in FIGS. 6B-6D.

Figures 6B, 6D:
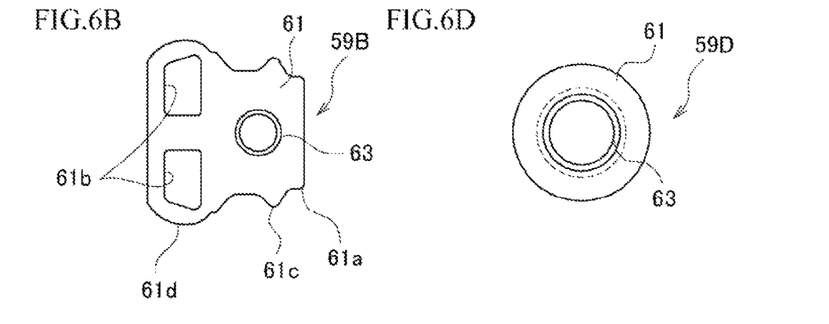

Similar to the base plate 59A, the base plates 59B, 59C, and 59D of FIGS. 6B-6D have plate bodies 61 and bosses 63, respectively. The base plates 59A, 59B, and 59C have rounded corners 61a. The base plates 59B and 59C have holes 61b for weight reduction. The base plate 59B has widthwise projections 61c. The base plates 59B and 59C have rounded sides 61d and 61e.

Accordingly, the mesh size of the mesh drum 13 is set in view of the corners 61a, the widthwise projections 61c and the like.

When feeding workpieces to the feeder stage 5, workpieces, for example, each being any one kind of the base plates 59A, 59B, 59C and 59D are charged into the mesh drum 13. The mesh drum 13 is driven to be rotated and tilted by the stepping motors 35 and 45. In addition, two or more kinds of base plates may be charged into the mesh drum 13.

The mesh drum 13 is operated according to the following setting.

Initial angle: 80 degrees, Finished angle: 100 degrees, Rotational speed: 2.3 degrees/second, Tilting back speed: 0.1 degrees/second The setting for the operation may be changed according to a desired discharge rate or a kind of workpieces. The initial angle and the finished angle are based on the vertical direction.

With the aforementioned setting, the part feeder 1 controls the stepping motors 35 and 45 so that about 5-30 pieces of the workpieces are discharged to the feeder stage 5 and then the stepping motors 35 and 45 are stopped.

This control is performed through monitoring of a camera. The part feeder 1 may control the stepping motors 35 and 45 according to an estimated relation between the remaining number of the workpieces and the rotational speed and the tilt angle of the mesh drum 13.

Figure 7:
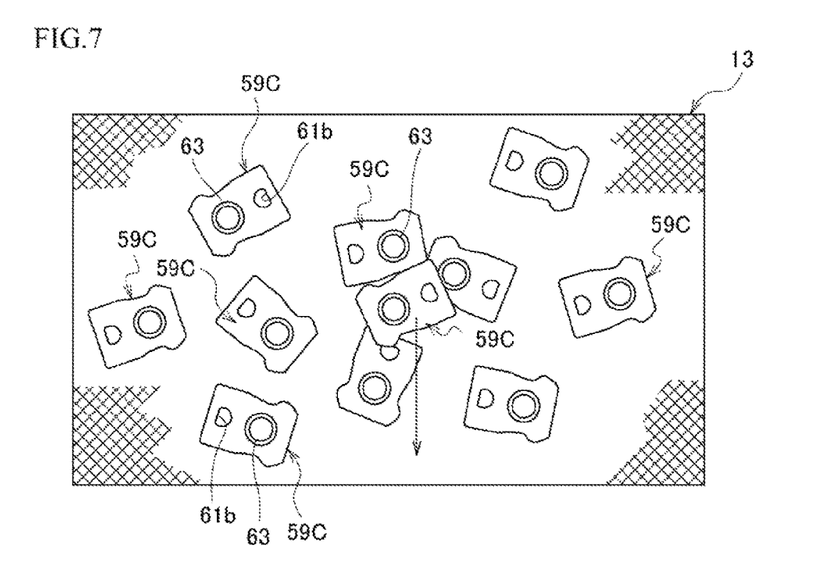
FIG. 7 is a development view partly illustrating a mesh circumferential wall of the mesh drum as well as workpieces according to the embodiment.

FIG. 7 is a development view partly illustrating the mesh circumferential wall 53 together with the workpieces in the mesh drum 13. In FIG. 7, the base plates 59C are used as the workpieces.

As illustrated in FIG. 7, base plates 59C directly contacting the mesh of the mesh circumferential wall 53 or the mesh drum 13 receive proper frictional force from the mesh drum 13.

The base plates 59C laid on the other base plates 59C in the mesh drum 13 slides down as indicated an arrow according to the rotation of the mesh drum 13. In FIG. 7, the upper side is the front side in the rotation direction of the mesh drum 13.

At the same time, the slid-down base plates 59C move toward the opening 19 of the mesh drum 13 according to the tilt of the mesh drum 13.

The part feeder 1, therefore, discharges the base plates 59C by a small amount at a fixed rate to the feeder stage 5 by adjusting the rotation around the axis and the tilt angle of the mesh drum 13.

The base plates 59C directly contacting the mesh of the mesh drum 13 are discharged to the feeder stage 5 as the tilt angle is gradually increased.

Contaminants or fine particles generated during the rotation of the mesh drum 13 pass through the mesh of the mesh drum 13 and are removed outside from the mesh drum 13.

Figure 8:
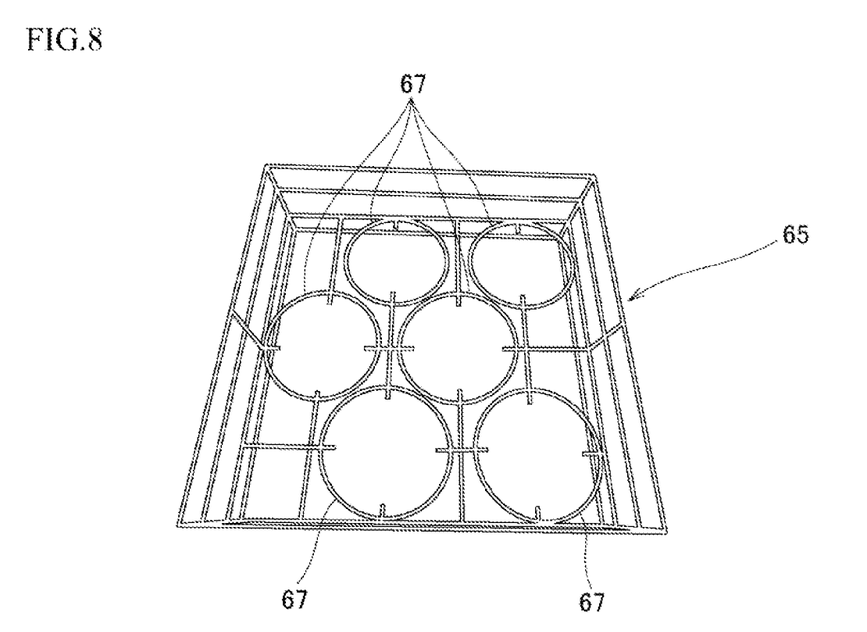
FIG. 8 is a perspective view illustrating a cleaning frame according to the first embodiment.
Figure 9:
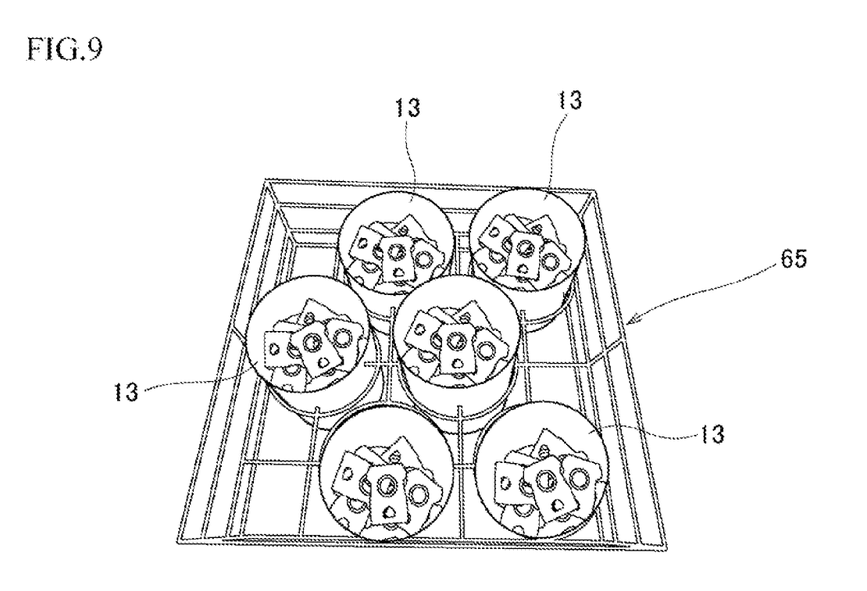
FIG. 9 is a perspective view illustrating the cleaning frame and the mesh drums supported with the cleaning frame according to the embodiment.
Figure 10:
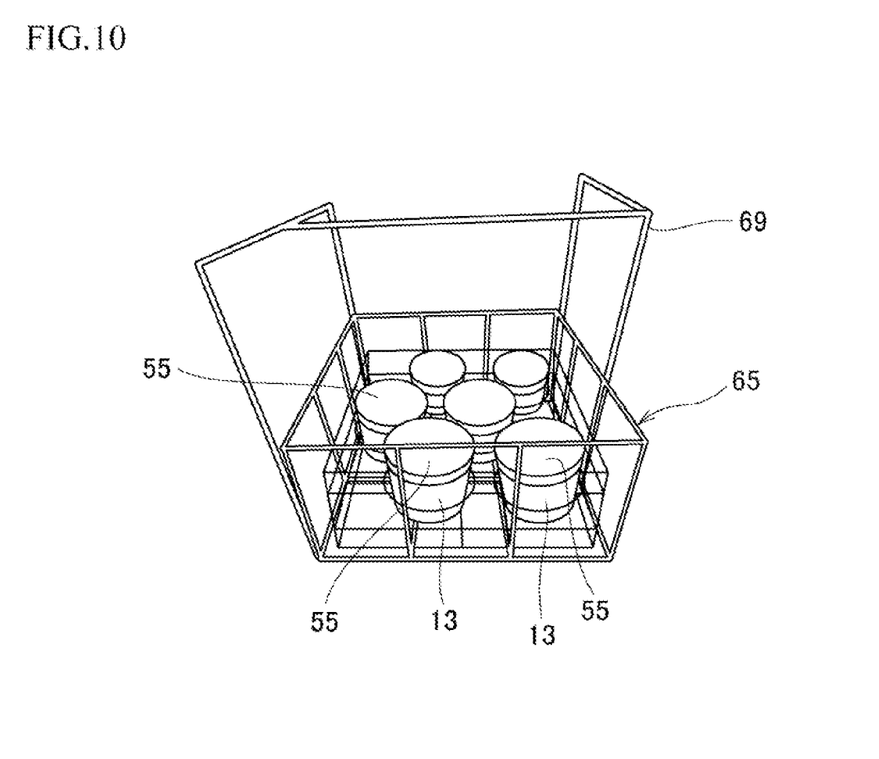
FIG. 10 is a perspective view illustrating the cleaning frame with a hanger and the mesh drums with the respective covers supported with the cleaning frame according to the embodiment.

FIG. 8 is a perspective view illustrating a cleaning frame, FIG. 9 is a perspective view illustrating the cleaning frame and the mesh drums supported with the cleaning frame, and FIG. 10 is a perspective view illustrating the cleaning frame with a hanger and the mesh drums with the respective covers. In FIG. 9, the base plates 59C are larger than in reality in order to be easily understood.

The cleaning frame 65 is made of, for example, metal wires and have support portions 67. The mesh drum 13 is detached from the drum base 11 to be set on the cleaning frame 65 and serve as the cleaning basket.

When using the mesh drum 13 as the cleaning basket, machined workpieces, for example, each being any one kind of the machined base plates 59A, 59B, 59C, and 59D are accommodated in the detached mesh drum 13. Then, the mesh drum 13 accommodating the base plates is supported with any one of the support portion 67 of the cleaning frame 65. With the other support portions 67, the other mesh drums 13 accommodating the base plates are also supported as illustrated in FIG. 9, respectively.

As illustrated in FIG. 10, the covers 55 are put on the respective mesh drums 13 and the hanger 69 is attached to the cleaning frame 65. Thereafter, the mesh drums 13 are immersed into a cleaning tank together with the cleaning frame 65 to conduct the ultrasonic cleaning to the workpieces or the base plates.

In this way, the ultrasonic cleaning is conducted to the workpieces or the base plates using the mesh drum 13 as the cleaning basket before a step of feeding the same to the feeder stage 5.

After the cleaning, the mesh drums 13 are pulled up from the cleaning tank and detached from the cleaning frame 65. The detached mesh drums 13 are fixed to the part feeder 1 one after another to feed the cleaned workpieces or the base plates to the feeder stage 5. When fixing the mesh drum 13, the cover 55 is removed.

As mentioned above, the part feeder 1 of the embodiment is provided with the mesh drum 13 with the mesh circumferential wall 53.

The mesh circumferential wall 53 of the mesh drum 13 properly applies the frictional force to the workpieces to suppress the workpieces from sliding on the mesh circumferential wall 53. The part feeder 1, therefore, discharges the workpieces from the mesh drum 13 by a small amount at a fixed rate to the feeder stage 5 by adjusting the rotation around the axis and the tilt of the mesh drum 13.

Namely, the workpieces or the base plates 59C directly contacting the mesh or the mesh circumferential wall 53 of the mesh drum 13 receives the proper frictional force whereas the base plates 59C laid on the other base plates 59C are preferentially slid down in the mesh drum 13 according to the rotation around the axis of the mesh drum 13. Further, since the mesh drum 13 has no blade on the inner circumferential surface, the workpieces are never laid on a blade unlike a conventional drum type hopper.

Accordingly, the part feeder 1 efficiently disperses the workpieces in the mesh drum 13 and accurately discharges the workpieces by a small amount at fixed rate to the feeder stage 5.

The contaminants or fine particles generated during the rotation of the mesh drum 13 pass through the mesh of the mesh drum 13 and are removed outside from the mesh drum 13.

The part feeder 1, therefore, prevents the contaminants generated in the mesh drum 13 from adhering the workpieces.

The mesh drum 13 is detachably supported with the apparatus base 41. In this embodiment, the drum part 3 has the drum base 11 being a part rotatably and tiltably connected to the apparatus base 41 and driven by the rotary drive 7 and the angle adjuster 9, the drum base 11 having the cylindrical shape to enclose the mesh drum 13 while maintaining the airgap between the mesh drum 13 and the drum base 11. The drum part 3 further has the engagement/disengagement part 21 fixing the opening 19 of the mesh drum 13 enclosed in the drum base 11 to the opening 15 of the drum base 11.

Accordingly, the mesh drum 13 is detached from the drum base 11 to serve as the cleaning basket. With this, the workpieces are completely or mostly prevented from becoming contaminated after the cleaning before the feeding.

The mesh drum 13 may be made of material other than the netlike member and may be made of a porous material shaped into a cylindrical drum which inner circumferential surface has a friction coefficient being the same as of the mesh drum 13 of the aforementioned embodiment.

The rotary drive may have rollers supported with a member on an apparatus base side and circumferentially supporting a drum base with the rollers, the member being configured to be tilted by an angle adjuster.

A stepping motor may be directly assembled to the rotary drive shaft of the drum base.

The material of the mesh drum 13 is not limited to specific material, but needs a friction coefficient of an inner circumferential surface of a mesh or the like relative to a workpiece higher than a friction coefficient between workpieces.

The engagement/disengagement part 21 may be arranged within the drum base 11.

The mesh drum 13 may be fixed to the drum base 11.

The drum part 3 may have only a mesh drum 13 without a drum base.

What is claimed is:

1. An apparatus of feeding workpieces, comprising:
   a mesh drum having a mesh circumferential wall that defines a space for accommodating workpieces, the mesh drum rotatably and tiltably supported with an apparatus base to separate and discharge the workpieces;
   a rotary drive that drives the mesh drum to be rotated;
   an angle adjuster that drives the mesh drum to be tilted;
   as drum base being a part rotatably and tiltably connected to the apparatus base and driven by the rotary drive and the angle adjuster, the drum base having a cylindrical shape to enclose the mesh drum while maintaining an airgap between the mesh drum and the drum base; and
   an engagement/disengagement part fixing an opening of the mesh drum enclosed in the drum base to an opening of the drum base,
   wherein
   the mesh drum has a mesh size of the mesh circumferential wall being set according to form of the workpieces to ensure the separating of the workpieces, and the mesh drum is detachably supported with the apparatus base.

* * * * *